United States Patent
Jagtap et al.

(12) 
(10) Patent No.: US 6,277,990 B1
(45) Date of Patent: Aug. 21, 2001

(54) SUBSTITUTED PHENANTHRIDINONES AND METHODS OF USE THEREOF

(75) Inventors: Prakash Jagtap, Beverly; Gary Southan, Salem; Andrew Salzman, Belmont; Csaba Szabo, Gloucester, all of MA (US)

(73) Assignee: Inotek Corporation, Beverly, MA (US)

( * ) Notice: Subject to any disclaimer, the term of this patent is extended or adjusted under 35 U.S.C. 154(b) by 0 days.

(21) Appl. No.: 09/454,867

(22) Filed: Dec. 7, 1999

(51) Int. Cl.⁷ .................. A61K 31/555; A61K 31/435; C07D 213/00; C07D 221/02; C07D 217/00
(52) U.S. Cl. ................... 546/1; 546/112; 546/139; 546/152; 514/187; 514/277
(58) Field of Search .................. 514/187, 277; 546/1, 112, 139, 152

(56) References Cited

U.S. PATENT DOCUMENTS

| | | | |
|---|---|---|---|
| 3,291,801 | * 12/1966 | Montgomery et al. | 514/258 |
| 3,932,643 | * 1/1976 | Gauthier et al. | 424/258 |
| 5,519,053 | 5/1996 | Kun | 514/457 |
| 5,583,155 | 12/1996 | Kun | 514/457 |
| 5,587,384 | 12/1996 | Zhange et al. | 514/309 |
| 5,621,104 | 4/1997 | Graham | 546/108 |
| 5,908,861 | 6/1999 | Kun | 514/456 |

FOREIGN PATENT DOCUMENTS

| | | |
|---|---|---|
| 99/11624 | * 3/1999 | (WO) . |
| WO99/11624 | 3/1999 | (WO) . |
| WO99/11645 | 3/1999 | (WO) . |

OTHER PUBLICATIONS

Andrievskii , et al., Chem. Heterocycl. Compds. (English Transl.), 21, 924–931 (1985).
Banasik, et al., J. Biol. Chem.. 267, 1569–1575 (1991).
Migachev, et al., D.L., Chem. Heterocycl. Compds. (Englsih Transl.), 17, 394–397 (1981).
Nemeth, et al., Eur. J. Pharmacol, 339, 215–221 (1997).
Szabo et al., Shock, 6, 79–88 (1996).
Szabo, et al., Trends Pharmacol. Sci., 19, 287–298 (1998).
Taylor, et al., J. Am. Chem. Soc., 78, 5104–5108 (1956).
Virag and Szabo, Br. J. Pharmacol., 126, 769–777 (1999).

* cited by examiner

Primary Examiner—Mukund J. Shah
Assistant Examiner—Sudhaker B. Patel
(74) Attorney, Agent, or Firm—Mintz,Levin, Cohn, Ferris, Glovsky and Popeo, P.C.; Ivor R. Elrifi, Esq.

(57) ABSTRACT

This invention provides a novel class of substituted 6(5H) phenanthridinone compounds. Pharmaceutical compositions, and methods of making and using the compounds, or a pharmaceutically acceptable salt, hydrate, prodrug, or mixture thereof are also described.

34 Claims, No Drawings

SUBSTITUTED PHENANTHRIDINONES AND METHODS OF USE THEREOF

FIELD OF THE INVENTION

The invention relates to substituted phenanthridinones.

BACKGROUND OF THE INVENTION

Inflammation disorders, such as arthritis, colitis, and autoimmune diabetes, typically manifest themselves as disorders distinct form those associated with reperfusion injury, e.g., stroke and heart attack, and can clinically manifest themselves as different entities. However, there can be common underlying mechanisms between these two types of disorders. In particular, inflammation and reperfusion injury can induce proinflammatory cytokine and chemokine synthesis. Induction of pro-inflammatory cytokines can, in turn, result in production of cytotoxic free radicals such as nitric oxide and superoxide. NO and superoxide can react to form peroxynitrite ($ONOO^-$) (Szabó et al., Shock 6:79–88, 1996).

The peroxynitrite-induced cell necrosis observed in inflammation and reperfusion injury involves, in significant part, the activation of the nuclear enzyme poly (ADP-ribose) synthetase (PARS). Activation of PARS is thought to be an important step in the cell-mediated death observed in inflammation and reperfusion injury (Szabó et al., Trends Pharmacol. Sci. 19: 287–98, 1998).

SUMMARY OF THE INVENTION

The invention is based in part on the discovery of novel substituted 6(5H)phenanthridinone derivatives and their unexpected effects in inhibiting inflammation and in treating reperfusion injuries.

Accordingly, in one aspect the invention provides novel substituted 6(5H)phenanthridinone derivatives falling within formula I, as set forth in the Detailed Description of the Invention, below.

Also provided is a method of treating inflammatory and reperfusion conditions in mammals by administering to a mammal in need of such treatment an effective amount of a compound according to formula I.

In a further aspect, the invention also includes a method for the production of compounds of formula I.

The substituted 6(5H)phenanthridinone compounds of the invention are potent, pharmaceutical compounds that can be used to treat a variety of conditions and diseases, typically those known to involve inflammatory mediator production and cell death.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

The present invention provides a novel class of 2-substituted 6(5H)phenanthridinone compounds falling within the formula I, as set forth below:

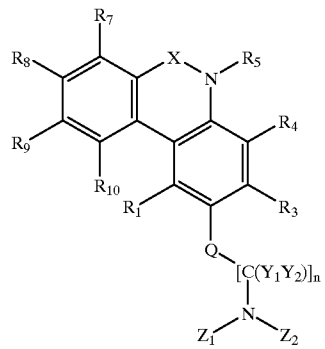

where
X is $C=O$, $C=S$, $SO_2$, $C=NH$, $C=NR_6$; C—Cl
Q is NHCO, O, CO, $OCO_2$, OCO, OCONH, $NR_2$, $NHCO_2$, S, $SO_2$, CS, SO;
$R_1$, $R_3$, $R_4$, $R_5$, $R_6$, $R_7$, $R_8$, $R_9$, $R_{10}$, are, independently, hydrogen or lower alkyl; halogen, nitro, amino, alkylamino, carboxy, ester
$Y_1$ and $Y_2$ are, independently: hydrogen, halo, alkylhalo, hydroxy, $C_1$–$C_{10}$ straight or branched chain alkyl, $C_2$–$C_{10}$ straight or branched chain alkenyl group, $C_3$–$C_8$ carbocyclic, aryl, alkylamino, amino, carboxy, ester, arylalkyl, nitro;
n is 0 to 10; and
$Z_1$ and $Z_2$ are, independently: hydrogen, alkylhalo, aklylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein the ring has 4–8 ring members.

In addition to the compounds of Formula I, the invention also provides a pharmaceutically acceptable base or acid addition salt, hydrate, ester, solvate, prodrug, metabolite, stereoisomer, or mixture thereof. The invention also includes pharmaceutical formulations comprising a compound of Formula I in association with a pharmaceutically acceptable carrier, diluent, or excipient.

As used herein:

"Alkyl" refers to saturated or unsaturated branched or straight chain hydrocarbon radical. Typical alkyl groups include methyl, ethyl, propyl, isopropyl, butyl, isobutyl, tertiary butyl, pentyl, hexyl and the like.

"Alkylhalo" refers an alkyl group containing a halogen substituent; "alkylhydroxy" refers to an alkyl group having a hydroxyl substituent; "alkylamino" refers to an alkyl group having an amino substituent; "alkylester" refers to an alkyl group having an ester functionality appended thereto; "alkylcarboxy" refers to an alkyl group having a carboxyl functionality appended thereto.

"Alkenyl" refers to unsaturated branched or straight chain hydrocarbon radical, having at least one carbon-carbon double bond.

"Alkynyl" refers to unsaturated branched or straight chain hydrocarbon radical having at least one carbon-carbon triple bond.

"Alkoxy" refers to the radical —O-alkyl. Typical alkoxy radicals are methoxy, ethoxy, propoxy, butoxy and pentoxy and the like.

"Cycloalkyl" refers to saturated monocyclic hydrocarbon radical containing 3–8 carbon atoms such as cyclopropyl, cyclobutyl, cyclopentyl, cyclohexyl, cycloheptyl, cyclooctyl, and the like.

"Aryl" refers to unsaturated cyclic, hydrocarbon radical.

"Substituted phenyl" refers to all possible isomeric phenyl radicals such as mono or disubstituted with a substituent selected from the group consisting of alkyl, alkoxy, hydroxy, or halo.

"Halo" refers to chloro, fluoro, bromo or iodo.

The carrier must be "acceptable" in the sense of being compatible with the active ingredient of the formulation and not deleterious to the subject to be treated. Preferably, the carrier is also capable of stabilizing the compound or composition.

Whenever the term "alkyl" or its prefix root appears in a name of a substituent (e.g. aralkoxyaryloxy) it shall be interpreted as including those limitations given above for "alkyl".

In some embodiments, X is C=O.

In some embodiments, one or more $R_1$, $R_3$, $R_4$, $R_5$, $R_6$, $R_7$, $R_8$, $R_9$, $Y_1$, or $Y_2$ are hydrogen.

In some embodiments, Q is NHCO.

In some embodiments, n is 1.

In some embodiments, one or both of $Z_1$ and $Z_2$ are methyl groups (PJ-34).

In some embodiments, one or both of $Z_1$ and $Z_2$ are ethyl groups (PJ-44).

In some embodiments, $Z_1$ is a methyl group and $Z_2$ is a benzyl group (PJ-45).

In some embodiments, N, $Z_1$ and $Z_2$ taken together, form piperidine, piperazine, N-alkylated or alkylcarbonylated piperazine, pyrole, imidazole, indole, or other $C_2$ to $C_{10}$ branched or cyclic or cycloalkenyl amines.

In some embodiments, $Z_1$, N, and $Z_2$ taken together form a fused ring having, six ring members.

In some embodiments, $Z_1$ and $Z_2$ taken together form —CH$_2$—CH$_2$—CH$_2$—CH$_2$—CH$_2$— (PJ-36).

In some embodiments, at least one of the ring members is oxygen.

In some embodiments, $Z_1$ and $Z_2$ taken together form —CH$_2$—CH$_2$—O—CH$_2$—CH$_2$— (PJ-38).

In some embodiments, two of the ring members are nitrogen atoms.

In some embodiments, $Z_1$ and $Z_2$ taken together form —CH$_2$—CH$_2$—N(CH$_3$)—CH$_2$—CH$_2$— (PJ-46).

In particularly preferred embodiments, the compounds have the structures represented by PJ 34, 36, 38, 44 and 46.

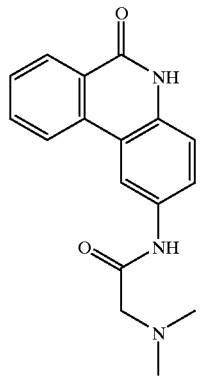

PJ34

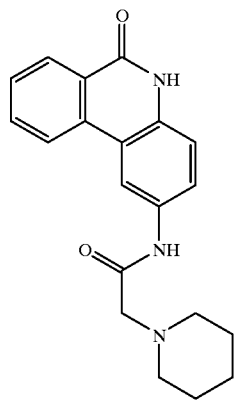

PJ36

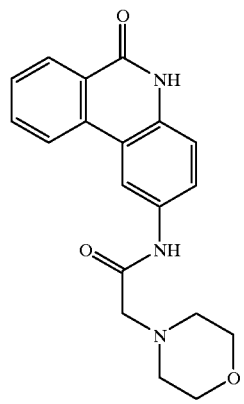

PJ38

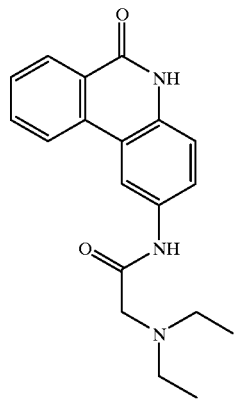

PJ44

-continued

PJ46

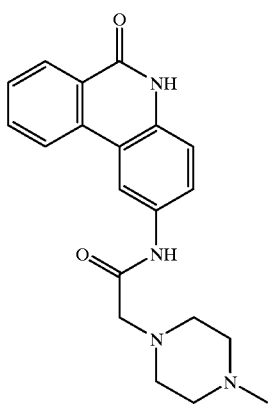

Salts encompassed within the term "pharmaceutically acceptable salts" refer to non-toxic salts of the compounds of this invention which are generally prepared by reacting the free base with a suitable organic or inorganic acid to produce "pharmaceutically-acceptable acid addition salts" of the compounds described herein. These compounds retain the biological effectiveness and properties of the free bases. Representative of such salts are the water-soluble and water-insoluble salts, such as the acetate, amsonate (4,4-diaminostilbene-2,2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

Methods of Using Substituted 6(5H) phenanthridinone Derivatives

The invention also includes a method of inhibiting poly (ADP)-ribose synthase activity (PARS) in a cell. This enzyme, which is also known as poly(ADP-ribose) synthetase and PARP (poly(ADP-ribose) polymerase, EC 2.4.99), and ADP-ribosyltransferase (ADPRT, EC 2.4.2.30), is a nuclear enzyme that catalyzes a transfer of the ADP ribose moiety of NAD+ to an acceptor protein.

The method includes contacting the cell with a compound of formula I in an amount sufficient to inhibit poly (ADP)-ribose-synthase in the cell. In general, any cell having, or capable of having, PARS activity, can be used. The can be provided in any form so long as it is accessible to the compound. For example, the cell can be provided in vitro, ex vivo, or in vivo. PARS activity can be measured using any method known in the art, e.g., methods as described in Banasik et al., *J Biol. Chem.* 267:1569–75, (1991).

Also provided in the invention is a method of inhibiting, preventing, or treating inflammation in a subject. The inflammation can be associated, e.g., with an inflammatory disease. Inflammatory diseases refer to diseases or conditions where there is an inflammation of the body tissue. These include local inflammatory responses and systemic inflammation. Examples of such diseases and conditions include: transplant rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gum, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases including diabetes mellitus, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used cancer chemotherapy.

The invention also includes a method of treating, preventing, or otherwise inhibiting reperfusion injury in a subject in need of treatment, prevention, or inhibition thereof. The method includes administering a compound of formula I in an amount sufficient to inhibit reperfusion injury in the subject. Reperfusion refers to the process whereby blood flow in the blood vessels is resumed after blood flow has been interrupted, such as occurs following constriction or obstruction of the vessel. Reperfusion is typically associated with ischemia and may result following a naturally occurring episode, such as a myocardial infarction or stroke, or during a surgical procedure where blood flow in vessels is purposely or unintentionally blocked off.

The subject in the above-mentioned methods can be, e.g. a mammal, e.g., a human, mouse, rat, dog, cat, horse, cow, pig, or non-human primate. Administration can be systemic or topical, and can be prophylactic or therapeutic.

The term "pharmacologically effective amount" means that amount of a drug or pharmaceutical agent that will elicit the biological or medical response of a tissue, system, animal or human that is being sought by a researcher or clinician.

The invention also includes pharmaceutical compositions suitable for inhibiting or preventing inflammation or reperfusion injury, PARS activity, or more than one of these activities. The compositions are preferably suitable for internal use and include an effective amount of a pharmacologically active compound of the invention, alone or in combination, with one or more pharmaceutically acceptable carriers. The compounds are especially useful in that they have very low, if any toxicity.

In practice, the compounds or their pharmaceutically acceptable salts, are administered in amounts which will be sufficient to inhibit inflammatory conditions or disease and/or prevent the development of inflammation or inflammatory disease in animals or mammals, and are used in the pharmaceutical form most suitable for such purposes.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Administration of the active compounds and salts described herein can be via any of the accepted modes of administration for therapeutic agents. These methods include systemic or local administration such as oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active compound or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as vetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One approach for parenteral administration employs the implantation of a slow-release or sustained-released systems, which assures that a constant level of dosage is maintained, according to U.S. Pat. No. 3,710,795, incorporated herein by reference.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the present invention range from 0.002 mg to 50 mg per kg of body weight per day.

Compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Any of the above pharmaceutical compositions may contain 0.1–99%, preferably 1–70% of the active compounds, especially compounds of the Formula I as active ingredients.

Synthesis of Novel Phenanthridinones

The substituted 6(5H)phenanthridinone compounds described herein can be prepared by methods well known in the art. Additional exemplary synthetic routes for compounds having the general structure of formula II, which describes compounds encompassed by Formula I, are illustrated as Scheme I and Scheme II, below.

In Scheme I, a 9-fluorenone (A) is treated with sulfuric acid and aqueous sodium azide in a ring-expansion, or Schmidt, reaction to produce 6(5H)-phenanthridinone (B). Nitration of (B) produces 2-nitro-6(5H)-phenanthridinone (C) as a major product, which is then reduced by Fe, $NH_4Cl$ and DMF, or catalytic dehdrogenation, to produce 2-amino-6($^5$H)-phenanthridinone (D). In general, a compound falling within Formula II is prepared by modifying the parent molecule 6(5H)-Phenanthridinone. See, e g., U.S. Pat. Nos. 3,291,801 and 3,932,643; Taylor et al., *J. Am. Chem. Soc.* 78:5104–5108 (1956). The 2-nitro (Compound C)- and 2-amino (Compound D)-6(5H)-phenanthridinones are synthesized by a slight modification of procedures described in Andrievskii, et al., *Chem. Heterocycl. Compds (English Transl.)* 21:8, 924–931 (1985), and Migachev, et al. *Chem. Heterocycl. Compds (English Transl.)* 17:3, 394–397 (1981).

Compound (E) is generated by acylating compound (D) with an appropriate halo-acylhalide. A compound falling within Formula II is then formed by the addition of a secondary amine.

In Scheme II, 2-amino-9-fluorenone (compound (F)) is acylated with a halo-acylhalide to produce the N-acylated compound (G). The central ring of compound (G) is then expanded in a Schmidt reaction as described for Scheme I. The ring opening reaction produces a mixture of compounds: the 2-substituted compounds according to Formula II are the major component of the mixture, while the 8-substituted compounds (H) are the minor component of the mixture.

Scheme 1

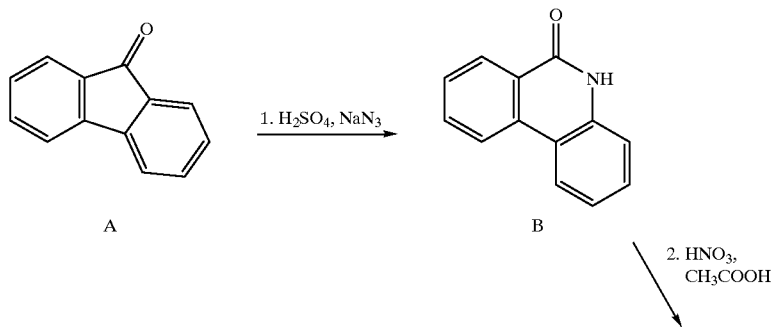

2. $HNO_3$, $CH_3COOH$

-continued
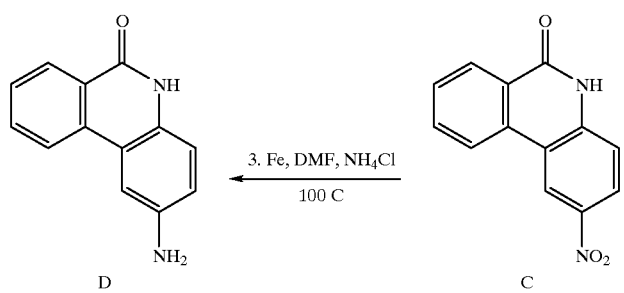
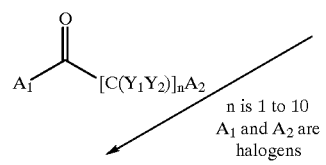
n is 1 to 10
$A_1$ and $A_2$ are halogens
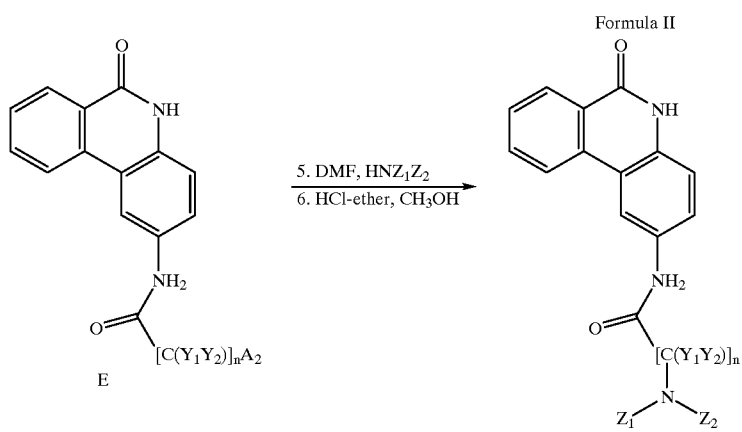
Scheme II
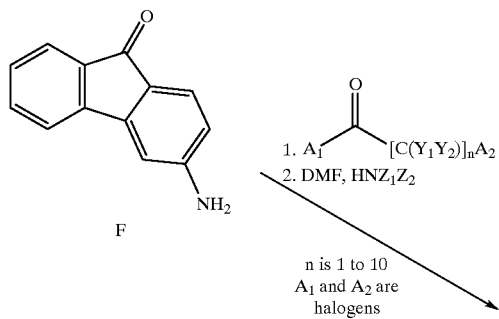
n is 1 to 10
$A_1$ and $A_2$ are halogens

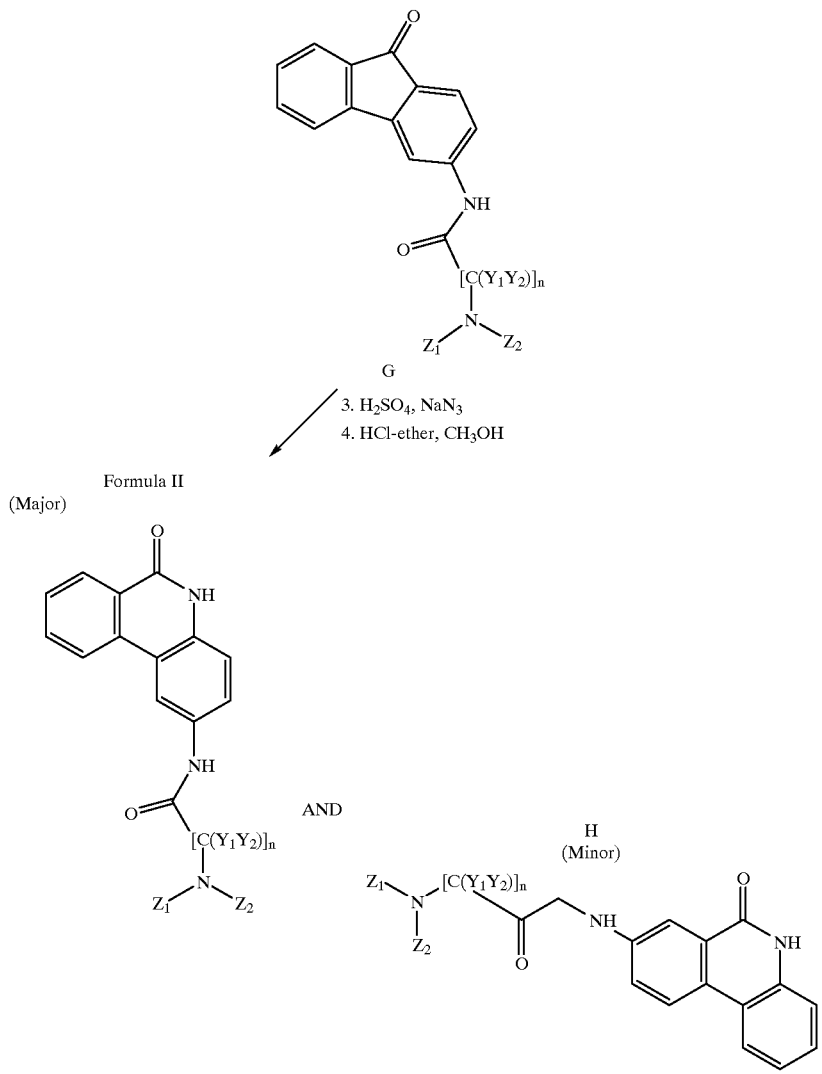

EXAMPLES

The invention will be further described in the following examples, which do not limit the scope of the invention described in the claims. The following examples illustrate the synthesis of novel substituted 6(5H)phenanthridinone derivatives of the invention and of their use to inhibit inflammation and reperfusion.

EXAMPLE 1

Synthesis of Novel Substituted Phenanthridinones (Scheme I).

Synthesis of 6(5H)-phenanthridinone: 6(5H)-Phenanthridinone was prepared by the method described by Gauthier in U.S. Pat. No. 3,932,643. Briefly, to a well stirred solution of 9-fluorenone (15 g, 0.083 mol) in concentrated sulfuric acid (500 mL), sodium azide (8.1 g, 0.12 mol) was slowly added over a period of 3 hr at 0° C. The reaction mixture was stirred at room temperature for 2 hr, until nitrogen no longer evolved. The reaction mixture was then poured slowly over crushed ice, to produce a solid precipitate which was filtered and washed thoroughly with cold water to remove sulfuric acid. The solid was then dried under vacuum, to give pure 6(5H)-phenanthridinone (15 g, 93%).

Synthesis of 2-Nitro-6(5H)-phenanthridinones 2-Nitro and 2-amino-6(5H)-phenanthridinones were synthesized by slight modification in the procedure described by Andrievskii et al., *Chem. Helerocycl. Compds (English Transl.)* 21:8, 924–931 (1985) and by Migachev et al., *Chem. Heterocycl. Compds (English Transl.)* 17:3, 394–397 (1981). Briefly, to a well stirred solution of 6(5 H)-phenanthridinone (4.5 g, 0.023 mol) in acetic acid (200 mL) nitric acid (10 mL) was added, and the reaction mixture was stirred at 100° C. for 2 hr. The solid that separated out was filtered and washed thoroughly with acetic acid and then by cold water to remove acidic impurities. The solid was then dried under vacuum, then recrystalized from DMF to give pure 2-nitro-6(5H)-phenanthridinone (3.8 g, 70%). The filtrate was diluted with cold water, and a yellow colored solid precipitated which was filtered and washed with water. The yellow solid was then dried under vacuum, and identified to be pure 4-nitro-6(5H)-phenanthridinone (650 mg, 12%).

Synthesis of 2-Amino-6(5H)-phenanthridinones: To a suspension of 2-nitro-6(5H)-phenanthridinone (3.8 g, 0.0 16 mol) in DMF (200 mL) was added an ammonium chloride solution (3%, 200 mL), followed by the addition of iron powder (22 g). The reaction mixture was stirred at 100° C. for 1 hr. The residue was removed by filtration, and the filtrate was made acidic by adding dilute HCl (25%, 20 mL). A solid separated from the solution and was filtered and washed thoroughly with cold water to remove acidic impurities. The solid was then dried under vacuum, to give hydrochloride salt of 2-amino-6(5H)-phenanthridinone (3.4 g, 89%).

Synthesis of N-(6-oxo-5,6-dihydro-phenanthridin-2-yl)-chloroacetamide: To a suspension of HCl salt of 2-amino-6(5H)-phenanthridinone (3.4 g, 0.014 mol) in ethyl acetate (200 mL) was added saturated solution of sodium bicarbonate (200 mL), followed by addition of chloroacetyl chloride (5.6 mL, 0.07 mol). The reaction mixture was stirred at room temperature for 2 days. The solid that separated out was filtered and washed thoroughly with cold water. It was then dried under vacuum to give N-(6-oxo-5,6-dihydro-phenanthridin-2-yl)-chloroacetamide (3.35 gm, 85%).

According to the methods illustrated above, by changing the identity of the secondary amine, a number of different N,N-disubstituted compounds were produced. Representative compounds are shown in Table 1.

TABLE 1

| Compound | N | $Y_1$ | $Y_2$ | $Z_1$ | $Z_2$ |
|---|---|---|---|---|---|
| PJ-34 | 1 | H | H | —$CH_3$ | —$CH_3$ |
| PJ-44 | 1 | H | H | —$CH_2CH_3$ | —$CH_2CH_3$ |
| PJ-36 | 1 | H | H | —$CH_2CH_2CH_2CH_2CH_2$— | |
| PJ-38 | 1 | H | H | —$CH_2CH_2OCH_2CH_2$— | |
| PJ-46 | 1 | H | H | —$CH_2CH_2N(CH_3)CH_2CH_2$— | |

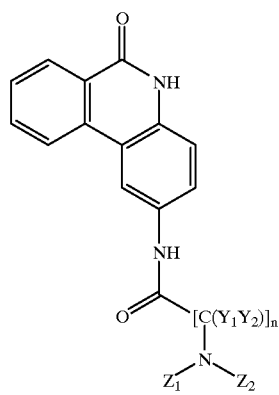

EXAMPLE 2

Alternate Synthesis of Novel Substituted Phenanthridinones (Scheme II).

Synthesis of N-(6-oxo-5,6-dihydro-phenanthridin-2-yl)-choroacetamide: To a suspension of the HCl salt of 2-amino-6(5H)-phenanthridinone (100 mg, 0.04 mmol) in DMF (5 mL), pyridine (0.5 mL) was added, followed by the addition of chloroacetyl chloride (0.2 mL, 0.002 mol) at 0° C. The reaction mixture was stirred at room temperature for 1 to 2 hrs. It was then poured over crushed ice, and the solid obtained was washed thoroughly with cold water. The solid was then dried under vacuum to give N-(6-oxo-5,6-dihydro-phenanthridin-2-yl)-choroacetamide (95 mg, 84%).

Synthesis of N-(6-oxo-5-6-dihydro-phenantridin-2-yl)-N,N-dimethylacetamide: To a solution of N-(6-oxo-5,6-dihydro-phenanthridin-2-yl)-chloroacetamide (1.5 g, 0.0052 mol) in DMF (10 mL) a solution of dimethyl amine in methanol (20 mL) was added. The reaction mixture was stirred at room temperature for 3 hours. The solid that separated out was filtered and washed thoroughly with cold water. It was then dried under vacuum and recrystalized from methanol/ether to give N-(6-oxo-5,6-dihydro-phenanthridin-2-yl)-N,N-dimethylacetamide. This compound was dissolved in methanol (25 rub) and treated with a solution of HCl in ether (2 M, 5 mL). The solid was filtered and washed thoroughly with dry ether, and recrystalized from methanol/ether to provide the hydrochloride salt of N-(6-oxo-5, 6-dihydro-phenanthridin-2-yl)-N,N-dimethylacetamide (1.4 g, 81%).

Synthesis of 2-(N-chloroacetyl)-9-fluorenone: A saturated solution of sodium bicarbonate (5 mL) was added to a solution of 2-amino-9-fluorenone (190 mg. 0.97 mmol) in ethyl acetate (5 mL). Next, chloroacetyl chloride (0.4 mL, 4.8 mmol) was added, and the reaction mixture was stirred at room temperature for 1 hour. The ethyl acetate layer was separated, and washed thoroughly with cold water. It was then dried under vacuum to give 2-N-chloroacetyl)-9-fluorenone (185 mg, 70%).

Synthesis of 2-[N-(2-N,N-dimethylaminoacetyl)]-9-fluorenone: To a solution of 2-(N-chloroacetyl)-9-fluorenone (185 mg, 0.68 mmol) in DMF (5 mL) a solution of dimethyl amine in methanol (5 mL) was added. The reaction mixture was stirred at room temperature for 1 hour. The reaction mixture was then poured over crushed ice and extracted in ethyl acetate (25 mL), washed thoroughly with cold water, dried over $Na_2SO_4$ then evaporated under vacuum to give 2-[N-(2-N,N-dimethylaminoacetyl)]-9-fluorenone (190 mg, 99%).

Synthesis of N-(6-oxo-5,6-dihydro-phenanthridin-2-yl)-N,N-dimethylacetamide: To a well stirred solution of 2-[N-(2-N,N-dimethylaminoacetyl)]-9-fluorenone(190 mg, 0.67 mmol) in concentrated sulfuric acid (5 mL), sodium azide (45 mg, 1.2 mmol) was added at 0° C., and the reaction mixture was stirred at room temperature until nitrogen no longer evolved. The reaction was then poured slowly over an ice-cold $K_2C_3$ solution, followed by extraction with ethyl acetate (25 mL). The ethyl acetate layer was washed thoroughly with cold water, dried over sodium sulfate, and concentrated under vacuum. The resulting residue was purified by PTLC (silica gel, 1000 μM) to give a mixture of N-(6-oxo-5,6-dihydro-phenanthridin-8-yl)-N,N-dimethylacetamide (52 mg, 26%) and N-(6-oxo-5,6-dihydro-phenanthridin-2-yl)-N,N-dimethylacetamide (78 mg, 39%).

EXAMPLE 3

Effects of Substituted Phenanthridinones on in vitro Inflammation Models

In in vitro studies, J774 macrophages were exposed to bacterial lipopolysaccharide (LPS), to induce pro-inflammatory mediator production and cytotoxicity. In this assay, the PJ compounds tested (PJ 34, 36, 38, 44 and 46) inhibited the production of the pro-inflammatory cytokine tumor necrosis factor alpha (TNF-α), the production of the pro-inflammatory chemokines macrophage inhibitory factor-1α and -2 (MIP-1α and MIP-2), as well as the production of the pro-inflammatory free radical nitric oxide (or NO, measured here as nitrite). Furthermore, the compounds restored the viability of the cells, which was suppressed in response to LPS exposure. This assay (the LPSstimulated macrophage) represents an in vitro model of an inflammatory situation. Agents that block inflammatory mediator production in this assay are expected to have anti-inflammatory or immunosuppressive effects in inflammatory or immune diseases.

The half-maximal inhibitory effect (in μM) of various PJ compounds was assessed under a variety of conditions in immunostimulated J774 macrophages and in peroxynitrite-stimulated thymocytes. Macrophages or thymocytes were first treated with a chosen PJ compound for 30 min at a concentration ranging from 0.1 to 30 μM. The cells were then immunostimulated with LPS (10 μg/ml) or treated with peroxynitrite (30 μM). MIP production in the macrophages was measured at 3 h, TNF and nitric oxide were measured at 24 h, cell viability in the macrophages were measured at 24 h. PARS activation and cell death in thymocytes were measured at 6 h. Measurements of mediator production, PARS activation and cell death were essentially as described in Németh, et al., Eur J Pharmacol 339:215–221 (1997) and Virág and Szabó, Br J Pharmacol, 126: 769–777 (1999). Results in Table 2 are shown as EC50 values (half maximal inhibition of mediator production or restoration of cell viability; in μM): [mean±SEM of n=3–6 determinations].

effect of the compounds in a systemic inflammatory model induced by bacterial lipopolysaccharide. Injection of bacterial lipopolysaccharide (LPS), at high doses, causes multiple organ dysfunction resembling of septic shock, and ultimately death. Agents that inhibit inflammatory mediator production, PARS activation, and cell death in this model, will prevent mortality induced by LPS. In experiments in Balb/c mice, injection of 90 mg/kg LPS intraperitoneally caused death in 92% of the animals over 24 h, whereas pretreatment of the animals with 20 mg/kg PJ34 reduced the endotoxin-induced mortality to 50% under the same experimental conditions. In response to an even higher dose of LPS (120 mg/kg), PJ 34, 36, 38, 44 and 46, all injected at 10 mg/kg every 6 hours) caused an improvement in the endotoxin-induced mortality from 70% death to 30–40% death over 24 hours.

These data indicate that the PJ series of compounds have therapeutic effects in various systemic and local inflammatory conditions.

EXAMPLE 6

Effect of Substituted Phenanthridinones on in vivo Reperfusion Injury Models

In order to substantiate the efficacy of the PJ series of compounds in ischemia-reperfusion conditions, we tested

TABLE 2

|  | Inhibition of TNF-α (J774) | Inhibition of MIP-1α (J774) | Inhibition of MIP-2 (J774) | Inhibition of Nitrite (J774) | Enhancement of cell Viability (J774) | Inhibition of PARS activation (thymocyte) | Enhancement of cell viability (thymocyte) |
| --- | --- | --- | --- | --- | --- | --- | --- |
| PJ34 | 5.4 ± 0.6 | 10.2 ± 1.4 | 7.2 ± 0.88 | 15.2 ± 2.8 | 12.5 ± 1.4 | 0.3 ± 0.1 | 0.2 ± 0.1 |
| PJ36 | 11.2 ± 1.1 | 15.2 ± 2.1 | 21.2 ± 2.7 | 25.4 ± 2.9 | 20.2 ± 2.3 | 0.2 ± 0.1 | 0.3 ± 0.1 |
| PJ38 | 6.2 ± 0.42 | 11.3 ± 1.4 | 14.9 ± 1.3 | 20.2 ± 1.5 | 22.1 ± 2.7 | 0.8 ± 0.2 | 0.4 ± 0.2 |
| PJ44 | 11.1 ± 0.67 | 10.2 ± 0.95 | 22.4 ± 1.2 | No effect | 16.2 ± 1.9 | 0.3 ± 0.1 | 0.2 ± 0.1 |
| PJ46 | 9.2 ± 0.88 | >30 | >30 | >30 | >30 | 1 ± 0.3 | 1.3 ± 0.3 |

EXAMPLE 4

Effects of Substituted Phenanthridinones on in vitro Reperfusion Injury Models

In additional in vitro studies in isolated thymocytes, cells were exposed to peroxynitrite or hydrogen peroxide (toxic oxidant species) to induce cytotoxicity. There is now evidence that in this system, the toxicity is, at least in part, related to activation of the nuclear enzyme PARS (see Introduction). In this assay, the compounds tested (PJ 34, 36, 38, 44 and 46) inhibited the activation of PARS. Furthermore, the compounds prevented the oxidant-induced suppression of the viability of the cells (Table 2). The current assay (the oxidant-stimulated thymocyte) represents an in vitro model of a situation where cells are dying because of exposure to pro-oxidant species, as it occurs in during the reperfusion of ischemic organs. In a second experimental system (oxygen/glucose deprivation induced cell death in cultured neurons, i.e. an in vitro, reductionist model of stroke), PJ34 provided significant cytoprotection (up to 70%) in the concentration range of 10 nM-1 μM. Agents that block PARS activation or cell death in this assay are expected to have cytoprotective effects in various diseases associated with reperfusion of ischemic organs.

EXAMPLE 5

Effect of Substituted Phenanthridinones on in vivo Inflammation Models

In order to substantiate the efficacy of the PJ series of compounds in inflammatory conditions, we have tested the the effect of the compounds in a local model of reperfusion injury induced by ligation and release of the coronary artery in the anesthetized rat. In a model of 1 hour coronary ischemia, followed by reperfusion for 1 hour, treatment with PJ 34 (5, g/kg i.v., injected 10 mm prior to the start of reperfusion), reduced myocardial infarct size development from 62±1 to 50±3% (area of necrosis, over area of risk). In addition, plasma levels of creatine phosphokinase (CPK, an indicator of myocardial necrosis) were reduced by PJ34 treatment by approx. 50%.

In another model, we utilized a mouse model of ischemic and reperfused gut. The superior mesenteric artery was occluded for 45 mm, followed by a reperfusion for 1 h. Following the end of the reperfusion, gut permeability was measured with the PD4 method in evened gut sacks. Ischemia-reperfusion increased the permeability of the gut from 9±2 to 135±27 ml/min/cm$^2$, indicating of severe damage of the reperfused gut. Treatment with PJ34 (5, g/kg i.v., injected 10 mm prior to the start of reperfusion), reduced the increase in the permeability of the gut to 41±12 mlmin/cm$^2$, indicating maintenance of the gut function. The ischemia-reperfusion studies in the gut were associated with a 38% mortality, whereas 100% survival was noted in the animals treated with PJ34. Similar protection was also observed with treatment with PJ36.

In another set of experiments, we have tested the effect of PJ34 in a rat model of middle cerebral artery occlusion/reperfusion. Occlusion lasted for 2 hours, followed by reperfusion for 24 hours. Infarct size was quantified with the tetrazolium staining, and survival and neurological scores were monitored. PJ34 was administered at 10 mg/kg i.v. 5 min before the start of reperfusion in one group, and 2 h after the beginning of reperfusion in another group. Vehicle-treated animals developed a 73% mortality over 24 hours, whereas no animals died in the drug treated groups. PJ34, given at the time of reperfusion or 2 h after the start of reperfusion reduced the size of brain infarction by 74±6 and 55±8%, respectively. Vehicle treated animals that survived for 24 h developed severe neurological deficit (4 on a scale of 1–4), whereas in the animals treated with PJ34 no detectable deficit was observed.

These data indicate that the PJ series of compounds have therapeutic effects in various systemic and local conditions of ischemia-reperfusion.

OTHER EMBODIMENTS

It is to be understood that while the invention has been described in conjunction with the detailed description thereof, the foregoing description is intended to illustrate and not limit the scope of the invention, which is defined by the scope of the appended claims.

What is claimed is:
1. A compound of formula I:

I:

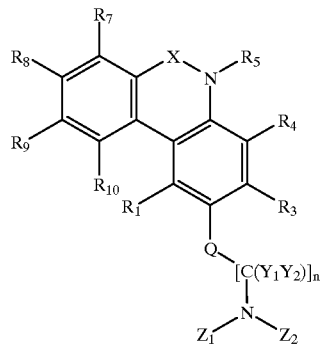

or a pharmaceutically acceptable base or acid addition salt, hydrate, ester, solvate, prodrug, metabolite, stereoisomer, or mixtures thereof, wherein:

X is C=O;
Q is NHCO;
$R_1$, $R_3$, $R_4$, $R_5$, $R_7$, $R_8$, $R_9$, $R_{10}$, are, independently, hydrogen or lower alkyl;
$Y_1$ and $Y_2$ are hydrogen;
n is 0 to 10; and
$Z_1$ and $Z_2$ are, independently: hydrogen, alkylhalo, alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members.

2. The compound of claim 1, wherein $R_1$, $R_3$, $R_4$, $R_5$, $R_6$, $R_7$, $R_8$, $R_9$, $Y_1$, and $Y_2$ are hydrogen.

3. The compound of claim 1, wherein n is 1.

4. The compound of claim 3, wherein $Z_1$ and $Z_2$ are methyl groups.

5. The compound of claim 3, wherein $Z_1$ and $Z_2$ are ethyl groups.

6. The compound of claim 3, wherein $Z_1$ and $Z_2$ are isopropyl groups.

7. The compound of claim 3, wherein $Z_1$ is a methyl group and $Z_2$ is a benzyl group.

8. The compound of claim 3 wherein N, $Z_1$ and $Z_2$, taken together, form a piperidine ring.

9. The compound of claim 3, wherein $Z_1$, N, and $Z_2$ taken together form a fused ring having six ring members.

10. A method of inhibiting poly(ADP)-ribose synthase activity in a cell, the method comprising contacting said cell with a compound of formula I in an amount sufficient to inhibit poly (ADP)-ribose-synthase in said cell:

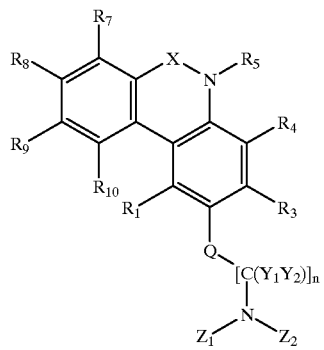

or a pharmaceutically acceptable base or acid addition salt, hydrate, ester, solvate, prodrug, metabolite, stereoisomer, or mixtures thereof, wherein:

X is C=O;
Q is NHCO;
$R_1$, $R_3$, $R_4$, $R_5$, $R_7$, $R_8$, $R_9$, $R_{10}$, are, independently, hydrogen or lower alkyl;
$Y_1$ and $Y_2$ are hydrogen;
n is 0 to 10; and
$Z_1$ and $Z_2$ are, independently: hydrogen, alkylhalo, aklylhydroxy, $C_1$–$C_{10}$ straight or branched chain alkyl, $C_2$–$C_{10}$ straight or branched chain alkenyl group, $C_2$–$C_{10}$ straight or branched chain alkynyl group, aryl, benzyl, alkylamino, alkylcarboxy, alkylester, arylalkyl, or $Z_1$ or $Z_2$ taken together form a fused ring, wherein said ring has 4–8 ring members.

11. The method of claim 10, wherein $R_1$, $R_3$, $R_4$, $R_5$, $R_6$, $R_7$, $R_8$, $R_9$, $Y_1$, and $Y_2$ are hydrogen.

12. The method of claim 10, wherein n is 1.

13. The method of claim 12, wherein $Z_1$ and $Z_2$ are methyl groups.

14. The method of claim 12, wherein $Z_1$ and $Z_2$ are ethyl groups.

15. The method of claim 12, wherein $Z_1$ and $Z_2$ are isopropyl groups.

16. The method of claim 12, wherein $Z_1$ is a methyl group and $Z_2$ is a benzyl group.

17. The method of claim 12, wherein N, $Z_1$ and $Z_2$, taken together, form a piperidine ring.

18. The method of claim 3, wherein $Z_1$, N, and $Z_2$ taken together form a fused ring having six ring members.

19. A method of treating or preventing local or systemic inflammation in a subject, the method comprising administering the compound of claim 1 in an amount sufficient to inhibit inflammation in said subject.

20. The method of claim 19, wherein said subject is a human subject.

21. The method of claim 19, wherein administering is systemic.

22. The method of claim 19, wherein administering is topical.

23. The method of claim 19 where said local inflammatory condition is caused by an inflammatory disorder of a joint, an inflammatory bowel disease, an inflammatory lung disorder, an inflammatory disease of the central nervous system, or an inflammatory disease of the eye.

24. The method of claim 19 where said systemic inflammatory condition is caused by a condition selected from the group consisting of gram-positive shock, gram negative shock, hemorrhagic shock, anaphylactic shock, traumatic shock, and systemic inflammation and chemotherapeutic shock.

25. A method of treating or preventing reperfusion injury in a subject, the method comprising administering the compound of claim 1 in an amount sufficient to inhibit reperfusion injury in said subject.

26. The method of claim 25, wherein said compound is administered prophylatcically.

27. The method of claim 25, wherein said compound is administered therapeutically.

28. The method of claim 25, wherein said reperfusion injury is myocardial infarction.

29. The method of claim 25, wherein said reperfusion injury is stroke.

30. The method of claim 25, wherein said subject is a human subject.

31. The method of claim 25, wherein administering is systemic.

32. The method of claim 25, wherein administering is topical.

33. A method of making a modified phenanthridinone, the method comprising:

(a) providing a salt of a 2-amino-6(5H)-phenanthridinone having the structure of compound III:

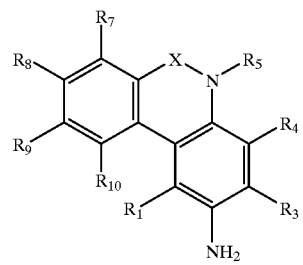

wherein:
  X is C=O;
  $R_1$, $R_3$, $R_4$, $R_5$, $R_7$, $R_8$, $R_9$, $R_{10}$ are, independently hydrogen or lower alkyl, and;
  n is 0 to 10;

(b) acetylating said 2-amino-6(5H)-phenanthridinone with a haloacetyl halide under conditions which allow for the formation of N-(6-oxo-5,6-dihydro-phenanthridin-2-yl-haloacetamide; and (c) reacting said N-(6-oxo-5,6-dihydro-phenanthridin-2-yl-haloacetamide with $HNZ_1Z_2$ under conditions which allow for the formation of N-(6-oxo-5,6-dihydro-phenanthridin-2-yl)-N,N-$Z_1Z_2$acetamide, thereby forming a modified phenanthridinone.

34. The method of claim 31, wherein $Z_1$ and $Z_2$ are, independently, alkoxy, hydrogen, halo, alkylhalo, hydroxy, $C_1$–$C_{10}$ straight or branched chain alkyl, $C_2$–$C_{10}$ straight or branched chain alkenyl group, aryl, alkylamino, amino, carboxy, ester, arylalkyl, nitro, or $Z_1$, N, and $Z_2$ taken together form a fused ring, wherein said ring has 4–8 ring members.

* * * * *